(12) United States Patent
Barak

(10) Patent No.: US 8,496,455 B2
(45) Date of Patent: Jul. 30, 2013

(54) ADMINISTRATION SET WITH TWO KEYS

(75) Inventor: Swi Barak, Caesarea (IL)

(73) Assignee: Caesarea Medical Electronics Ltd. (IL)

( * ) Notice: Subject to any disclaimer, the term of this patent is extended or adjusted under 35 U.S.C. 154(b) by 1516 days.

(21) Appl. No.: 11/964,043

(22) Filed: Dec. 25, 2007

(65) Prior Publication Data

US 2008/0199337 A1  Aug. 21, 2008

(30) Foreign Application Priority Data

Dec. 25, 2006 (IL) .......................................... 180305

(51) Int. Cl.
*F04B 43/08* (2006.01)
*F04B 43/12* (2006.01)
*F04B 45/06* (2006.01)

(52) U.S. Cl.
USPC ....................................................... 417/477.2

(58) Field of Classification Search
USPC ............................ 417/477.2, 477.13; 604/153
See application file for complete search history.

(56) References Cited

U.S. PATENT DOCUMENTS

| | | | | |
|---|---|---|---|---|
| 5,437,635 A | * | 8/1995 | Fields et al. | 604/65 |
| 5,869,774 A | * | 2/1999 | Backlund et al. | 73/864.34 |
| 6,083,206 A | * | 7/2000 | Molko | 604/253 |
| 6,213,738 B1 | * | 4/2001 | Danby et al. | 417/478 |
| 6,224,578 B1 | * | 5/2001 | Davis et al. | 604/247 |
| 6,248,093 B1 | * | 6/2001 | Moberg | 604/131 |
| 6,261,262 B1 | * | 7/2001 | Briggs et al. | 604/153 |
| 2002/0127114 A1 | * | 9/2002 | Barak | 417/12 |
| 2002/0177821 A1 | * | 11/2002 | Barak | 604/251 |
| 2003/0014035 A1 | * | 1/2003 | Trombley et al. | 604/500 |
| 2004/0022655 A1 | * | 2/2004 | Knuth et al. | 417/477.1 |

* cited by examiner

*Primary Examiner* — Devon Kramer
*Assistant Examiner* — Amene Bayou

(57) ABSTRACT

A flow set for administration of liquid when using a liquid pump is disclosed. The flow set of the present invention permits identification of the flow set by a liquid pump that uses this flow set and prevention of pumping tube-segment over stretching.

16 Claims, 4 Drawing Sheets

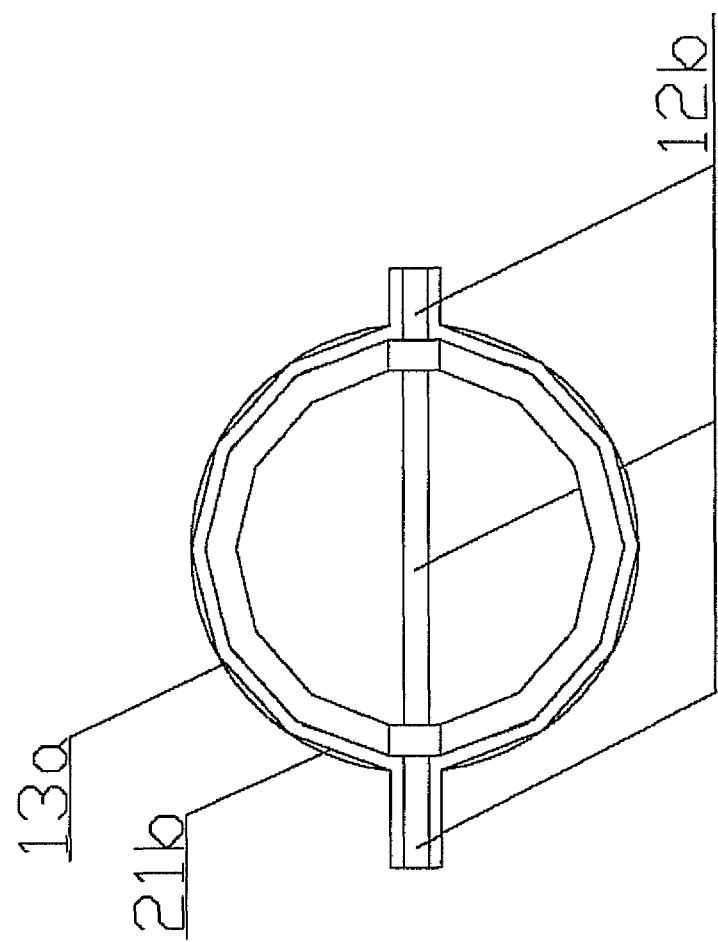

ADMINISTRATION SET WITH TWO KEYS

CLAIM FOR PRIORITY

This application claims priority from Israeli Application No. 180305 filed on Dec. 25, 2006 and is fully incorporated by reference as if fully set forth herein.

FIELD OF THE INVENTION

This invention relates to liquid administration and more specially, it is concerned with a liquid flow set useful for administration of liquids to a patient through a flexible tube.

BACKGROUND OF THE INVENTION

Systems for administration of liquids to a patient are widely known. However, a variety of different pumps are available for propelling liquid to a patient, which may differ, among others, by construction and safety of use.

Flow sets for use with a liquid pump must attentively design for safe use. A dedicated tube-segment of the tube must be installed in the pump and the tube must be installed in the right place, tighten, straight and stretched only up to a determined value. The flow set must be full with liquid before using it and should remain full as long as it in used. Moreover, the pumping tube-segment must be replaced by other tube-segment when it losses its flexibility.

From U.S. Pat. No. 4,798,590 a flow set became known, comprising a drip chamber, a flexible plastic line, having a roller clamp, an inlet connector coupled to an end of a pump chamber, wherein the other end of the pump chamber is coupled to an outlet connector. The outlet connector is coupled through a line having a roller clamp and a Y-site therein a luer.

The present invention is concerned with a liquid flow set that includes a number of safety features in order to identify such a flow set by the liquid pump that uses it and also to prevent the pumping tube-segment from over stretching.

SUMMARY OF THE INVENTION

There are broadly contemplated herein, in accordance with at least one presently preferred embodiment of the present invention, arrangements for administration of liquid by using a liquid pump.

In summary, one aspect of the invention provides a disposable flow set comprising: (a) a drip chamber or a spike; (b) a first administration tube to administer liquid from said drip chamber or spike; (c) at least one pumping tube-segment, connected to the first administration tube, enabling said flow set to be installed in a liquid pump; (d) a second administration tube installed at the end of the last one of said pumping tube-segment; (e) an anti free flow valve installed on the second administration tubing; and (f) at least one identifying key.

Another aspect of the invention provides a disposable flow set comprising: (a) a drip chamber; (b) a first administration tube to administer liquid from said drip chamber; (c) at least one pumping tube-segment, connected to the first administration tube, enabling said flow set to be installed in a liquid pump; (d) a second administration tube installed at the end of the last one of said pumping tube-segment; (e) an anti free flow valve installed on the second administration tubing; (f) at least one identifying key, whereby the at least one pumping tube-segment has a respective identifying-key connected thereto; and (g) at least one stretching key, whereby the at least one pumping tube-segment has a respective stretching key connected thereto.

Furthermore, an additional aspect of the invention provides a disposable flow set comprising: (a) a spike; (b) a first administration tube to administer liquid from said spike; (c) at least one pumping tube-segment, connected to the first administration tube, enabling said flow set to be installed in a liquid pump; (d) a second administration tube installed at the end of the last one of said pumping tube-segment; (e) an anti free flow valve installed on the second administration tubing; and (f) at least one identifying key, whereby the at least one pumping tube-segment has a respective identifying-key connected thereto.

BRIEF DESCRIPTION OF THE DRAWINGS

FIG. 4 illustrates a cross section of a stretching key in accordance with the present invention.

DESCRIPTION OF THE PREFERRED EMBODIMENTS

Figure 1:
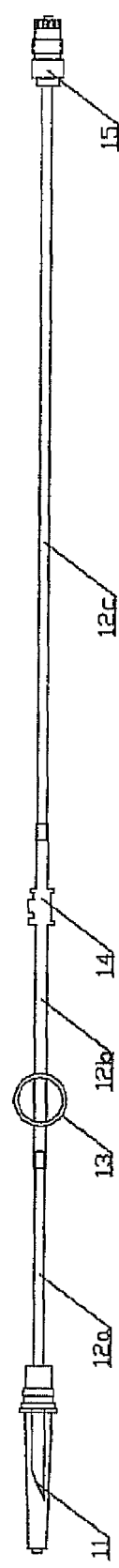
FIG. 1 illustrates a flowset in accordance with the present invention.

For a better understanding of the present invention, together with other and further features and advantages thereof, reference is made to the following description, taken in conjunction with the accompanying drawings, and the scope of the invention will be pointed out in the appended claims.

It will be readily understood that the components of the present invention, as generally described and illustrated in the Figures herein, may be arranged and designed in a wide variety of different configurations. Thus, the following more detailed description of the embodiments of the apparatus, system, and method of the present invention, as represented in FIGS. 1 through 4, is not intended to limit the scope of the invention, as claimed, but is merely representative of selected embodiments of the invention.

Reference throughout this specification to "one embodiment" or "an embodiment" (or the like) means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals or other labels throughout.

The following description is intended only by way of example, and simply illustrates certain selected embodiments of devices, systems, and processes that are consistent with the invention as claimed herein.

There is broadly contemplated herein, in accordance with at least one presently preferred embodiment of the present invention, a flow set for administration of liquid when using a liquid pump and for either identification by a liquid pump that uses this flow set and prevention of pumping tube-segment over stretching.

Flow sets for use with a liquid pump must attentively be designed for safe use. A dedicated tube-segment of the tube must be installed in the pump and the tube must be installed in the right place, correct direction, tightened, straight and stretched only to a determined degree. The flow set must be full with liquid before using it and should remain full as long as it is in use. Moreover, the pumping tube-segment must be replaced by another tube-segment when it losses its flexibility.

The flow set of the present invention preferably has a number of features that ensures the use of only this specific flow set in a compatible liquid pump. There is preferably an identifying-key that prevents the insertion of a wrong flow set and enables the liquid pump to determine the presence of the compatible administration set.

In addition, the flow set of the present invention preferably has a number of features that ensure the use of the flow set in a way that prevents pumping tube-segment from over stretching.

The principles and operation of the flow set according to the present invention, and the use of the flow set, may be better understood with reference to the drawings and the accompanying description.

Referring now to the drawings, FIG. 1 illustrates a flow set with a spike 11, a first administration tube 12a which administrates the liquid through pumping tube-segments 12b, a second administration tube 12c administrates the pumped liquid to an anti-free-flow valve 15. An identifying-key 14 is installed near one of the pumping tube-segment's ends. Following installation of the identifying key 14 in a liquid pump 21 the Stretching Key 13 is used to install the pumping tube-segment 12b in the liquid pump 21 in a correct position—tightened, straight and stretched up to the determined degree.

Figure 2:
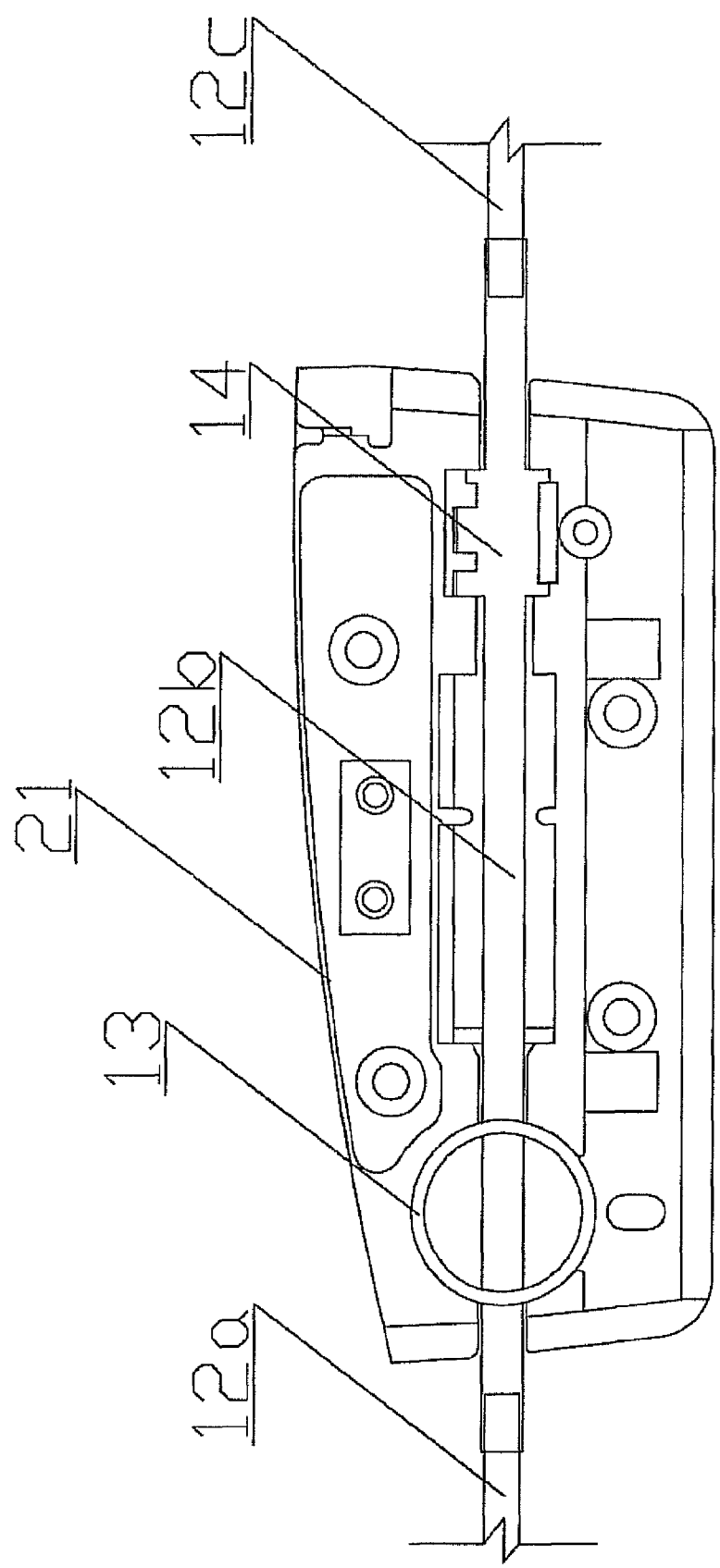
FIG. 2 illustrates the installation of a pumping tube segment of a flowset in a liquid pump in accordance with the present invention.

FIG. 2 illustrates the way to install a pumping tube-segment 12b in a liquid pump 21. An identifying-key 14 is installed on the pumping tube-segment 12b. The identifying-key 14 is clamped to the tube segment 12b and includes a number of teeth 14a. Each tooth has a specific width and specific location, creating a code that enables inserting the tube segment 12b only to a specific liquid pump 21 that has a set of niches 21a that are arranged in the same code. The identifying-key 14 has also a pressure plate 34b. This pressure-plate 34b is pressed by a door (not shown) of the liquid pump 21 and presses the pumping tube-segment 12b against a pressure sensor (not shown) that is installed in the liquid pump 21 behind the identifying-key 14. The identifying-key 14 prevents the liquid pump 21 from starting operation unless the pressure sensor measures a determined pressure. The Stretching Key is designed to be installed in a recess 21b of the liquid pump 21. The determined clamping distance and position between the identifying key 14 and the stretching key 13 will correspond to the respective distance and position between the identifying key niches 21a and the stretching key recess 21b in the liquid pump 21. When both the identifying key and the stretching key are installed in the liquid pump 21, the determined distance between their clamping locations on the pumping tube-segment 12b forces the pumping tube segment 12b to stay tightened, straight and stretched up to a determined degree.

Figure 3:
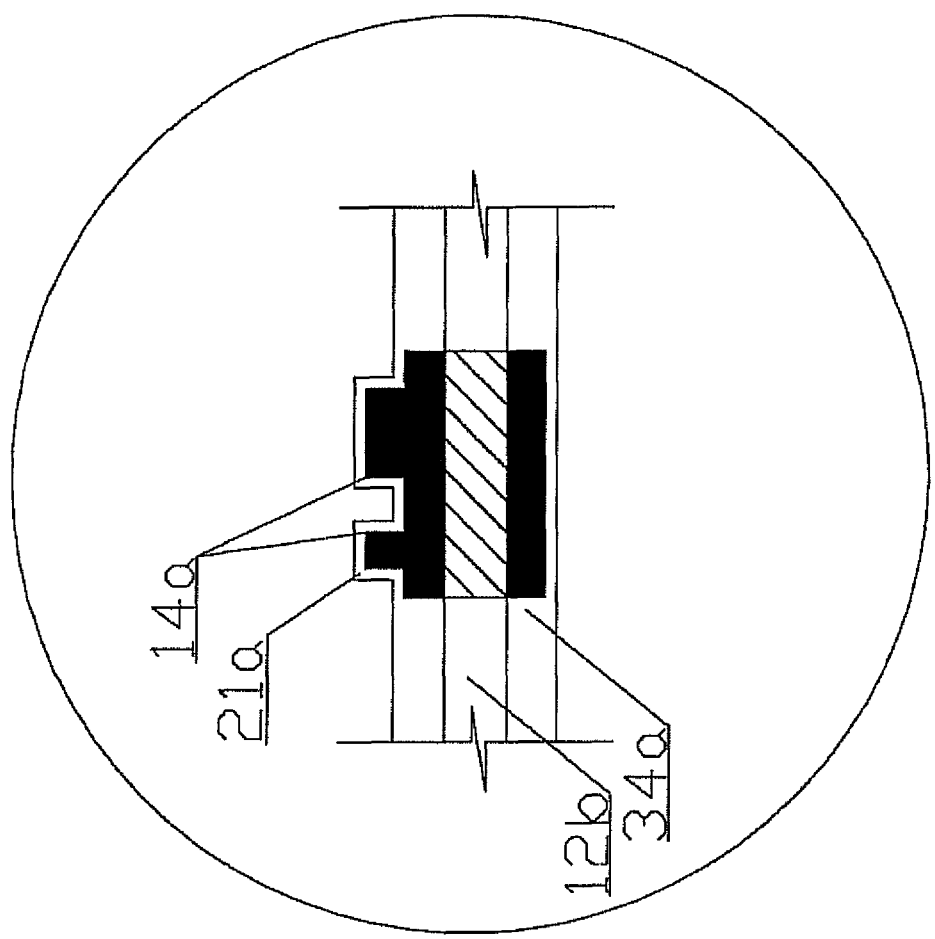
FIG. 3 illustrates a cross section of an identifying key in accordance with the present invention.

FIG. 3 illustrates a cross section of an identifying-key 14. The identifying-key 14 is clamped to the tube-segment 12b near one of its ends. The identifying key 14 includes a set of teeth 14a to enable the insertion of the flow set only into a compatible liquid pump and presses the pumping tube-segment 12b against a pressure sensor (not shown) of the liquid pump enabling the pressure measuring.

FIG. 4 illustrates a cross section of a stretching key 13. The stretching key 13 is clamped to the pumping tube-segment 12b near its other end. The stretching-key 13 may be ring shaped in order to enable an air sensor (not shown) to detect air in the tube segment part located in said stretching-key center. It also may cause the pumping tube-segment to be placed in front of the air sensor for optimal detection of air in the pumping tube-segment.

Although the invention has been described in conjunction with specific embodiments thereof, it is evident that many alternatives, modifications and variations will be apparent to those skilled in the art, accordingly it is intended to embrace all such alternatives modifications and variations that fall within scope of the appended claims.

What is claimed is:

1. A disposable flow set comprising:
   a) a drip chamber or a spike;
   b) a first administration tube to administer liquid from said drip chamber or spike;
   c) at least one pumping tube-segment, connected to the first administration tube, enabling said flow set to be installed in a liquid pump;
   d) a second administration tube installed at an end of said at least one pumping tube-segment;
   e) an anti free flow valve installed on the second administration tube;
   f) at least one identifying key which is connected to the at least one pumping tube-segment has a respective identifying key connected thereto; and
   g) at least one stretching key, whereby the at least one pumping tube-segment has a respective stretching key connected thereto; wherein said stretching key is ring shaped in order to allow detection of air in said pumping tube-segment by an air detector through a hole in said stretching key.

2. The disposable flow set of claim 1, wherein the at least one identifying-key comprises a hoop that is clamped on said at least one pumping tube-segment and includes:
   a) a number of teeth with a unique combination of location and width, said teeth being configured to be inserted into compatible niches in the liquid pump and prevent insertion of said flow set to a non compatible liquid pump; and
   b) a pressing-plate configured to allow said pumping tube segment to be pressed against a pressure sensor of said liquid pump enabling said liquid pump to use sensed pressure to verify existence of said flow set.

3. The flow set of claim 2, wherein each stretching key comprises a hoop that is clamped on the at least one pumping tube segment and includes:
   a) a unique pattern to be inserted into a compatible recess in the liquid pump that prevents insertion of the flow set into a non compatible liquid pump; and
   b) connection to the at least one pumping tube-segment at a determined distance from the identifying key.

4. The disposable flow set of claim 2, wherein the at least one identifying key is clamped to the at least one pumping tube-segment at a distance between 45 millimeters and 47 millimeters from the at least one stretching key also clamped to the at least one pumping tube-segment.

5. The disposable flow set of claim 2, wherein the teeth of the identifying key are arranged to correspond to the niches on the liquid pump.

6. The disposable flow set of claim 2, wherein the stretching key is of a size and shape that prevents a door to the liquid pump from closing if said stretching key is not placed in a recess of the liquid pump.

7. The disposable flow set of claim 2, wherein the identifying key is of a size and shape that prevents a door to the liquid pump from closing if said identifying key is not placed in the liquid pump niches.

8. The disposable flow set of claim 2, wherein the identifying key is pressed towards the liquid pump pressure sensor in order for a software of the liquid pump to verify that a door of the liquid pump is closed and the at least one pumping tubing-segment is present.

9. The disposable flow set of claim 2, wherein the stretching key centers the at least one pumping tube segment in front of the air detector of the liquid pump to assure air detection in the at least one pumping tube-segment.

10. The disposable flow set of claim 2, wherein an inside diameter of the at least one pumping tube-segment of the disposal flow set is between 2 millimeters and 4 millimeters.

11. The disposable flow set of claim 2, wherein at least one air detector is positioned behind the stretching key when the stretching key is installed in the liquid pump.

12. The disposable flow set of claim 2, wherein at least one air detector is positioned in front of the stretching key when the stretching key is installed in the liquid pump.

13. The disposable flow set of claim 2, further comprising: a controlling means in an inlet of the drip chamber, enabling control of volume of entering drops.

14. A disposable flow set comprising:
a) a drip chamber;
b) a first administration tube to administer liquid from said drip chamber;
c) at least one pumping tube-segment connected to the first administration tube enabling said flow set to be installed in a liquid pump;
d) a second administration tube installed at an end of said at least one pumping tube-segment;
e) an anti free flow valve installed on a second administration tube;
f) at least one identifying key which is connected to the at least one pumping tube segment has a respective identifying-key connected thereto; and
g) at least one stretching key, whereby the at least one pumping tube segment has a respective stretching key connected thereto; wherein said stretching key is adapted to position said pumping tube-segment to allow detection of air therein by an air detector through an opening in said stretching key.

15. The disposable flow set of claim 14, wherein the at least one identifying-key comprises a hoop that is clamped on said at least one pumping tube-segment and includes:
a) a number of teeth with a unique combination of location and width, said teeth being configured to be inserted into compatible niches in a specific the liquid pump and prevent insertion of said flow set to a non compatible liquid pump; and
b) a pressing-plate configured to allow said pumping tube-segment to be pressed against a pressure sensor of said liquid pump enabling said liquid pump to use the sensed pressure to verify existence of said flow set.

16. The flow set of claim 14, wherein each stretching key comprises a hoop that is clamped on the at least one pumping tube segment and includes:
a) a unique pattern configured to be inserted into a compatible recess in the liquid pump and to prevent insertion of the flow set to a non compatible liquid pump;
b) a connection to the at least one pumping tube-segment at a determined distance from clamping of the identifying key to said at least one pumping tube-segment.

\* \* \* \* \*